United States Patent [19]
Nardella

[11] Patent Number: 5,733,281
[45] Date of Patent: Mar. 31, 1998

[54] ULTRASOUND AND IMPEDANCE FEEDBACK SYSTEM FOR USE WITH ELECTROSURGICAL INSTRUMENTS

[75] Inventor: Paul C. Nardella, Wareham, Mass.

[73] Assignee: American Ablation Co., Inc., Taunton, Mass.

[21] Appl. No.: 619,829

[22] Filed: Mar. 19, 1996

[51] Int. Cl.$^6$ .................................................. A61B 17/36
[52] U.S. Cl. ........................................................ 606/38
[58] Field of Search .............................. 606/12, 34, 35, 606/38, 41, 42

[56] References Cited

U.S. PATENT DOCUMENTS

| | | | |
|---|---|---|---|
| 4,474,179 | 10/1984 | Koch | 128/303.17 |
| 4,576,177 | 3/1986 | Webster, Jr. | 128/660 |
| 4,727,874 | 3/1988 | Bowers et al. | 606/38 |
| 4,733,667 | 3/1988 | Olive et al. | 128/419 |
| 4,887,605 | 12/1989 | Angelsen et al. | 128/660.03 |
| 4,950,267 | 8/1990 | Ishihara et al. | 606/12 |
| 5,158,560 | 10/1992 | Sogawa et al. | 606/15 |
| 5,249,163 | 9/1993 | Erickson | 367/149 |
| 5,254,112 | 10/1993 | Sinofsky et al. | |
| 5,295,484 | 3/1994 | Marcus et al. | 128/660.03 |
| 5,316,000 | 5/1994 | Chapelon et al. | 128/660.03 |
| 5,334,193 | 8/1994 | Nardella | 606/41 |
| 5,342,357 | 8/1994 | Nardella | 606/40 |
| 5,368,037 | 11/1994 | Eberle et al. | 128/662.06 |
| 5,368,558 | 11/1994 | Nita | 604/22 |
| 5,377,685 | 1/1995 | Kazi et al. | 128/662.06 |

*Primary Examiner*—William E. Kamm
*Attorney, Agent, or Firm*—Nutter, McClennen & Fish, LLP

[57] ABSTRACT

An electrosurgical feedback system for detecting the effects of electrosurgical energy on tissue. The feedback system can include an acoustical detection element that acoustically detects the effects of energy on tissue and then generates an acoustic output signal indicative of these energy effects. A power regulation element, in response to the acoustic output signal, regulates the electrosurgical energy supplied to the tissue. Alternatively, the feedback system can include an impedance determination circuit that determines the impedance of the tissue. The tissue determination stage can include a first and second differentiator circuit to determine the time-based derivative of the measured tissue impedance. The tissue determination stage generates an impedance output signal of either the first or second derivative of the tissue impedance, which is conveyed to the power regulation element. The regulation element regulates the amount of energy supplied to the tissue in response to the impedance output signal.

34 Claims, 3 Drawing Sheets

ULTRASOUND AND IMPEDANCE FEEDBACK SYSTEM FOR USE WITH ELECTROSURGICAL INSTRUMENTS

BACKGROUND OF THE INVENTION

The present invention relates to electrosurgical feedback systems for electrosurgical tools, and more particularly to the use of impedance and acoustic feedback to regulate the application of energy to tissue.

Catheters for RF ablation are known and are commonly used to treat various diseases and medical disorders. Typically, the catheter mounts an energy-delivering electrode that is coupled to a source of RF energy, e.g., an electrosurgical generator. Other electrodes can be proximally positioned on the catheter and can be used for sensing and other related electrical purposes. The generator energizes the electrode, which then transfers the energy to tissue disposed adjacent thereto. The surgical energy is typically applied to the tissue at a selected level and for a selected duration to effect a biological change in the tissue.

In prior procedures, the ablation catheter is employed to alter tissue. In order to ablate the tissue, RF energy is applied to create a lesion via the energy-delivering electrode without regard to the specific level of RF energy supplied by the generator. In situations where too much RF energy is delivered to the tissue during the electrosurgical procedure, the tissue "pops", thus indicating the application of an excessive amount of energy.

In recent years, ablation catheters have been used to form deeper tissue lesions, e.g., lesions that extend beneath the tissue that is immediately adjacent to the catheter. One problem encountered during the treatment of tissue with ablation catheters is that the heating of the energy-delivering electrode can effect unwanted charring of tissue immediately adjacent to the catheter. One known solution to this problem is to pass a cooling fluid over the energy-delivering electrode. The cooling fluid serves to cool the electrode and thus prevent excess heating of tissue, while enabling the deeper penetration of electrosurgical energy.

A potential drawback of the use of ablation catheters to form deep lesions within tissue is the risk of supplying an excessive level of power to the energy-delivering electrode. The delivery of energy to a surgical site vaporizes fluids within tissue cells, thus generating steam within the cells. Upon further heating, the pressure associated with steam buildup within the cells can exceed the mechanical strength of the cell walls, thus causing the cells to explode.

It would thus be advantageous to develop a system for use with ablation catheters, and with electrosurgical instruments in general, that is able to detect the effects of energy on tissue to prevent the permanent destruction of tissue.

It is thus an object of the invention to provide an electrosurgical feedback system that detects and responds to the formation of gas within tissue during the electrosurgical procedure. Another object of the invention is to provide an electrosurgical feedback system that enables electrosurgical tools to be conveniently and safely utilized during the application of RF energy. Other general and more specific objects of the invention will in part be apparent from the drawings and description which follow.

SUMMARY OF THE INVENTION

This invention attains the foregoing and other objects with an electrosurgical feedback system that detects the effects of energy on tissue. The system includes a surgical tool that mounts a first energy-delivering electrode that is adapted to deliver power from a power source, e.g., an RF generator, to tissue disposed adjacent thereto. The system further includes an impedance measurement element in electrical communication with the surgical tool for determining the electrical impedance of the tissue. According to one embodiment, the impedance measurement element generates an impedance output signal indicative of the measured tissue impedance.

The system of the invention also includes a differentiation element for determining the derivative of the tissue impedance in response to the impedance output signal. The differentiation element preferably generates a derivative output signal indicative of the time-based derivative of the impedance output signal in response to the impedance signal. A power regulation element in circuit with the differentiation element and the power source regulates the application of power by the power source to the energy-delivering electrode in response to the derivative output signal.

According to one embodiment of the invention, the differentiation element includes first and second differentiation elements. The first differentiation element is in communication with the impedance measurement element and determines the first time-based derivative of the impedance output signal. The first differentiation element preferably generates a first derivative output signal in response to the impedance output signal. The second differentiation element is in circuit with the first differentiation element and the power regulation element and determines the second time-based derivative of the impedance output signal. The second differentiation element preferably generates a second derivative output signal in response to the first derivative output signal, and the power regulation element regulates the application of power to the energy-delivering electrode in response to the second derivative output signal.

According to another embodiment, the differentiation element includes a single differentiation element that is in communication with the impedance measurement element for determining the first time-based derivative of the impedance output signal. The first differentiation element generates a first derivative output signal in response to the impedance output signal. The pulse regulation element preferably regulates the application of power to the energy-delivering electrode in response to the first derivative output signal.

According to still another embodiment of the invention, the feedback system further includes an acoustical detection element, e.g., an ultrasonic transducer, coupled to the surgical tool and the pulse regulation element for acoustically detecting the effects of energy on tissue, such as the generation of steam created during the heating process. The acoustical detection element preferably generates an acoustic output signal, and the power regulation element preferably regulates the application of power to the energy-delivering electrode in response to either the derivative output signal or the acoustic output signal. The tern "acoustic" is intended to include any vibratory disturbance of any frequency in a selected fluid, such as air, and includes sonic and ultrasonic waves.

In another aspect, the feedback system includes a pulse element for electrically activating the ultrasonic transducer to emit ultrasonic pulses having a selected frequency and a selected duration. The emitted ultrasonic pulses are reflected either the by tissue or by the gas, e.g., steam, formed during the surgical procedure. The acoustical detection element further includes a receiver for generating an acoustic output signal in response to the reflected ultrasonic pulses. The reflected pulses are preferably displayed to a clinician by a display element.

According to another embodiment, the acoustical detection element can include a microphone for detecting sounds associated with the application of energy to tissue, and for generating an electrical output signal corresponding to the detected sounds. A speaker, coupled to the microphone element, preferably produces an audible output signal in response to the electrical output signal.

The feedback system further pertains to a system that includes a surgical tool upon which is mounted at least a first energy-delivering electrode that receives power from a power source and delivers power to tissue. An acoustical detection element is coupled to the surgical tool for detecting acoustically the effects of energy on the tissue. The acoustical detection element preferably generates an acoustic output signal indicative of the heating effects on the tissue.

The system of the invention further includes a power regulation element in circuit with the surgical tool and the acoustical detection element, e.g., an ultrasonic transducer, for regulating the power supplied to the energy-delivering electrode in response to the acoustic output signal.

According to one aspect, the acoustical detection element further includes a pulsing element that applies an electrical current to the transducer to induce the transducer to generate ultrasonic pulses. According to another aspect, a processor element is coupled to the acoustical element for receiving and processing electrical signals generated by the transducer that are indicative of the reflected ultrasonic pulses. The transducer then generates an acoustical output signal in response to the reflected pulses.

According to another aspect, an impedance measurement element can be coupled to the surgical tool for determining the impedance of the tissue disposed between the energy-receiving electrode and the second electrode. According to one practice, the impedance measurement element generates an impedance output signal indicative of the impedance of the tissue.

According to still another aspect, the system includes a first derivative element coupled to the impedance measurement element for determining the first time-based derivative of the impedance output signal, and for generating a first derivative output signal indicative of the first derivative of the tissue impedance. In yet another aspect, the first derivative output signal is conveyed to the power regulation element, which regulates the power supplied to the energy-delivering electrode in response to either the first derivative output signal or the acoustic output signal.

According to yet another aspect, a second derivative element determines the derivative of the first derivative output signal, and then generates a second derivative output signal indicative of the second derivative of the impedance output signal. The second derivative output signal is conveyed to the power regulation element, which regulates the power supplied to the energy-delivering electrode in response to either the second derivative output signal or the acoustic output signal.

According to another embodiment of the invention, the acoustical detection element can include a microphone for detecting the effect of energy on the tissue, where the microphone generates an electrical output signal indicative of sounds associated with the heating of tissue. Preferably, the microphone detects the creation of gas at the surgical site. The system can also include a speaker for converting the electrical output signal of the microphone into an audible output signal.

BRIEF DESCRIPTION OF THE DRAWINGS

The foregoing and other objects, features and advantages of the invention will be apparent from the following description and apparent from the accompanying drawings, in which like reference characters refer to the same parts throughout the different views.

DESCRIPTION OF ILLUSTRATED EMBODIMENTS

Figure 1:
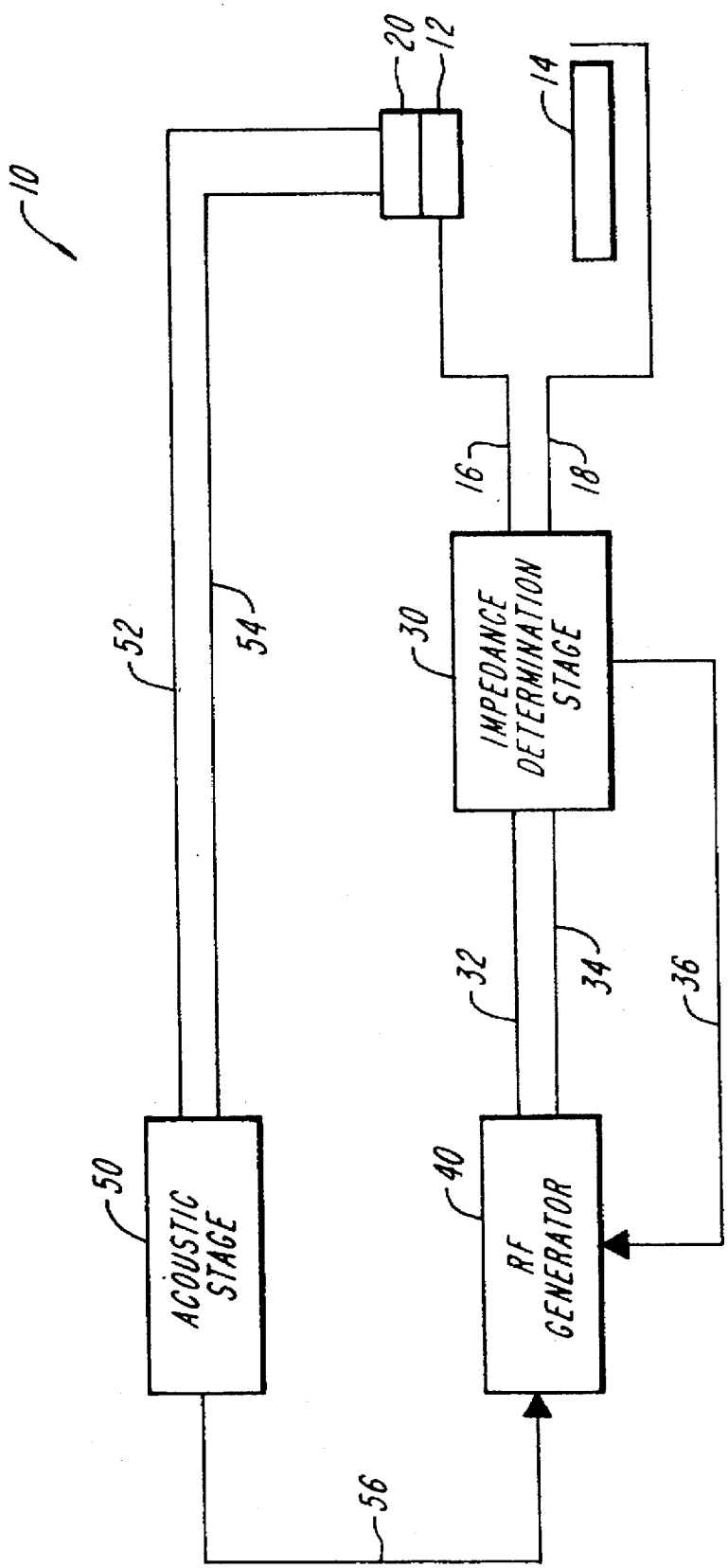
FIG. 1 is a block diagram illustrating an acoustic and impedance electrosurgical feedback system according to the present invention.

FIG. 1 illustrates an acoustic and impedance feedback electrosurgical system 10 constructed according to the invention. The system 10 includes an energy-delivering electrode 12 and a return electrode 14 that can be mounted upon a variety of surgical tools, such as ablation catheters, laproscopic and endoscopic tools and like surgical instruments. The energy-delivering electrode 12 can operate as a cutting edge and deliver electrosurgical energy to tissue disposed adjacent thereto. An ultrasonic transducer 20 is mounted proximal to the energy-delivering electrode 12. Ultrasonic transducers suitable for use with electrosurgical instruments are known and commerically available.

An impedance determination stage 30 is coupled to the electrodes 12 and 14 by a pair of electrical conductors 16 and 18. The impedance determination stage 30 determines the impedance of tissue disposed between the electrodes 12 and 14 and generates an impedance output signal which is conveyed to an electrosurgical generator 40 along electrical conductor 36. The generator 40 preferably supplies RF energy, e.g., electrosurgical energy to the electrodes 12 and 14 by way of the impedance determination stage 30 along electrical conductors 32 and 34. Electrode 14 can be a ground electrode to enable bipolar operation of the device, or can be a remote ground pad for monopolar operation. The impedance feedback signal generated by the impedance stage 30 preferably regulates the level of energy supplied by the generator 40 to the energy-delivering electrode 12.

An acoustic stage 50 is coupled to the ultrasonic transducer 20 by conductors 52 and 54. The acoustic stage induces the ultrasonic transducer 20 to resonate and thus produce ultrasonic waves. These waves are typically reflected by the tissue or other components in the vicinity of the tissue, e.g., steam or other gases, and are received by the transducer 20, which produces corresponding electrical signals that are received and processed by the acoustic stage 50. The acoustic stage preferably produces an acoustic output signal that is conveyed to the generator 40 along conductor 56. The acoustic output signal operates to regulate the level or amount of power supplied to the energy-delivering electrode 12. Those of ordinary skill will recognize that the acoustic stage 50 provides a separate feedback pathway from that of the impedance determination stage 30, and thus is operable alone or in conjunction with the impedance stage 30, as illustrated. The acoustic stage constituents and output signal are described in greater detail below.

Figure 2:
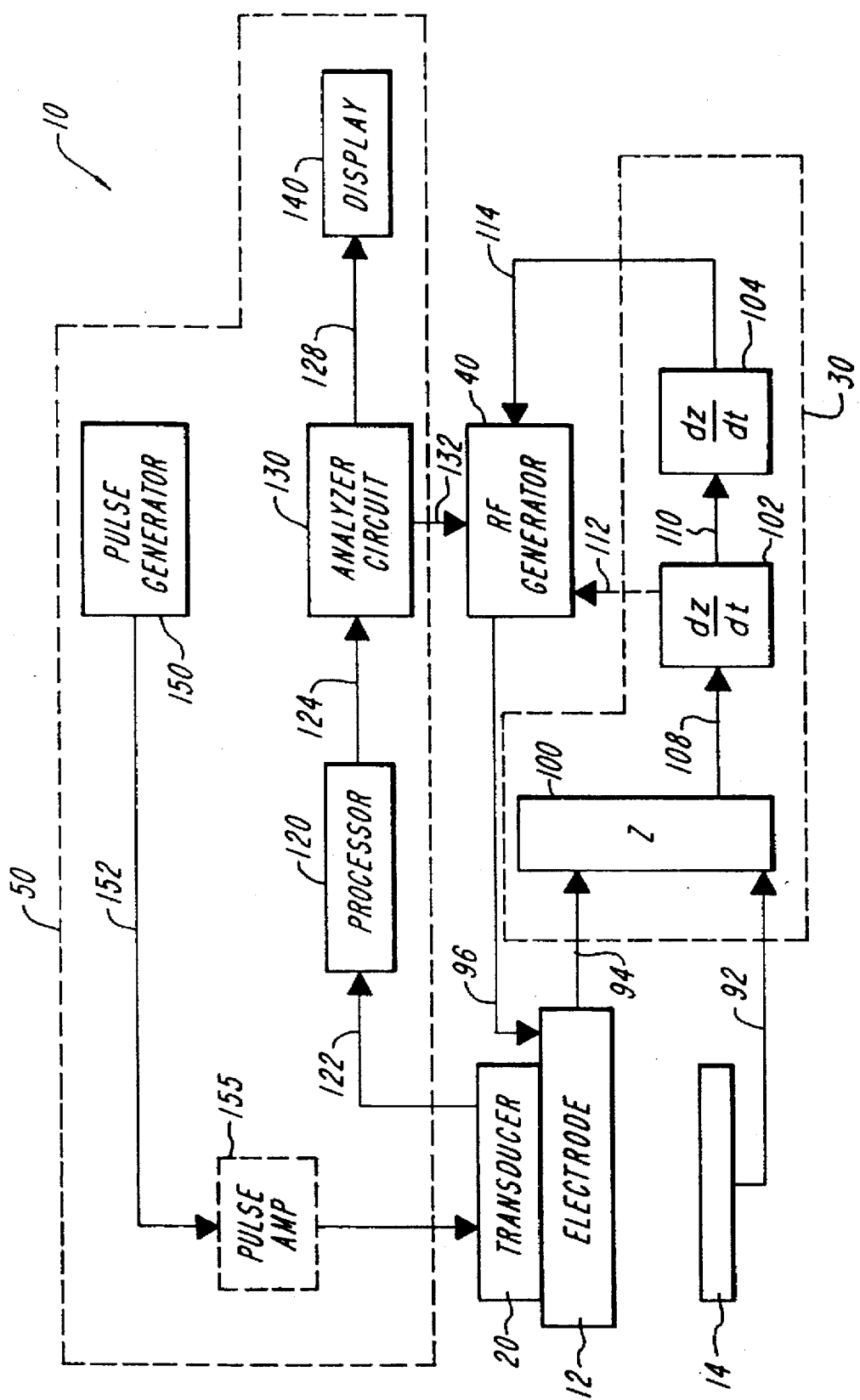
FIG. 2 is a more detailed schematic illustration of the acoustic and impedance feedback electrosurgical system of FIG. 1.

FIG. 2 is a detailed schematic representation of the electrosurgical feedback system 10 of the invention. The illustrated electrodes 12 and 14 can both be mounted on the surgical tool to form a bipolar device, or the electrode 14 can be configured as a remote ground pad for placement on a patient, thus forming a monopolar device, as previously described.

The illustrated impedance determination stage 30 includes an impedance monitor circuit 100, a first differentiator circuit 102, and a second differentiator circuit 104. The impedance monitor 100 is coupled to electrodes 12 and 14 by conductors 94 and 92, respectively. The monitor 100 determines the impedance of the tissue disposed between the two electrodes 12 and 14 by measuring the current and voltage therebetween. A simple arithmetic calculation performed by dedicated electronic circuitry known to those of ordinary skill determines the tissue impedance. The impedance monitor 100 then generates an output tissue impedance signal 'z' that is conveyed to the first differentiator circuit 102 along conductor 108.

The first differentiator circuit 102 determines the first time-rate derivative of the impedance output signal 'z', and generates in response to the impedance signal a first derivative output signal dz/dt indicative of the first time-based derivative of the impedance signal 'z'. The first derivative output signal dz/dt can be conveyed along feedback conductor 112 (illustrated in dashed lines) to generator 40. The output signal dz/dt can thus be employed to regulate or adjust the amount of electrosurgical RF energy supplied to the energy-delivering electrode 12 by the generator 40, thus regulating the amount of heat or energy applied to the tissue. The illustrated differentiator circuit 102 is known to those of ordinary skill, and can be comprised of either an integrated circuit or of other electrical or solid state components, such as an operational amplifier with associated resistors and capacitors.

The first derivative output signal dz/dt generated by the first differentiator circuit 102 contains information regarding the condition of the tissue at the surgical site, since the measured mechanical impedance of the tissue changes during the electrosurgical procedure. For example, the application of increasing levels of RF energy or the application of a constant level of RF energy to the tissue over a selected period of time leads first to the vaporization of intracellular fluid, blanching, desiccation and then ultimately bursting of the tissue. One natural by-product of the effects of electrosurgical energy on tissue is the creation of steam (or other gas), which is developed when the intracellular fluids are superheated by the applied energy. This generated steam and its associated pressure can cause severe tissue damage if allowed to accumulate within the tissue to excessive levels. Thus, determining and displaying (e.g., on an oscilloscope) the first derivative signal dz/dt during the electrosurgical procedure allows a clinician to monitor visually the changes in the measured tissue impedance caused by the changing condition of the tissue, and thus monitor the effective steam levels within the tissue. Consequently, the clinician can regulate the level of energy applied to the tissue to regulate the amount of steam generated therein, while concomitantly monitoring the tissue condition.

As is known, tissue is most effectively heated and cauterized by RF energy when the measured tissue impedance is kept within a preferred electrosurgical range of values, e.g., between about 20 ohms and about 300 ohms. Thus, when the measured tissue impedance is outside of a predetermined range of impedance values, the power supplied by the generator 40 to the electrode 12 can be regulated by either the clinician, via a switch or knob mounted on the generator or a foot pedal coupled thereto, or by dedicated power regulating circuitry, e.g., simple comparator circuitry that would be obvious to the ordinarily skilled artisan, and which can be integrated with the impedance measurement stage 30 and/or the generator 40.

Impedance readings outside of a preferred range of values or that exceed some selected criteria, such as readings above a selected value for a selected period of time, can also be indicative of the overall heating effects on the tissue. Consequently, the feedback system 10 can also be employed to regulate the power supplied to the electrode 12 to detect the specific effects of heating on the tissue, such as the creation of steam, and/or to control the overall heating effects. The term "regulate", used with respect to power, means to control, reduce, increase or eliminate the power supplied to the tissue via the energy-delivering electrode. The phrase "effects of energy or heating on tissue" refers to those changes that occur to the tissue when subjected to electrosurgical energy, including the generation of gases, such as steam, during the heating process.

According to an alternate embodiment of the invention, as illustrated in FIG. 2, the impedance determination stage 30 can include a second differentiator circuit 104. Preferably, the second differentiator circuit 104 is similar to or identical to the first differentiator circuit 102. The illustrated second differentiator circuit 104 is disposed electrically in circuit with the generator 40 and the first differentiator circuit 102, and is arranged to receive the first derivative output signal dz/dt along output conductor 110. The second differentiator circuit 104 preferably generates in response to the first derivative output signal dz/dt a second derivative output signal $d^2z/(dt)^2$ which corresponds to the second time-based derivative of the impedance signal 'z'. This second derivative output signal can be conveyed to the generator 40 along feedback conductor 114.

The illustrated second differentiator circuit 104 filters out the changes in the impedance slope of the characteristic impedance curve while concomitantly magnifying the presence of gases, e.g., steam, generated during the heating process. Thus, the second derivative output signal $d^2z/(dt)^2$ can be used as a feedback signal (1) to detect the presence and relative level of steam generated at the surgical site, and/or (2) to regulate the power supplied to the tissue by the generator 40. By regulating the power supplied to the energy-delivering electrode 12, the illustrated feedback system 10 can regulate the relative levels of steam to within a selected range, and preferably below that level that causes permanent and/or unwanted damage to the tissue. For example, if steam levels rise above a selected level, the power supplied to the electrode 12 can be regulated to allow at least a portion of the steam to be reabsorbed, and thus effectively removed from the surgical site. Hence, the use of feedback, e.g., the monitoring and adjusting of power during the procedure, prevents unwanted tissue damage associated with the excess production of steam.

In operation, the electrosurgical generator 40 supplies power to the energy-delivering electrode 12 along conductor 96, which heats tissue disposed between the electrodes 12 and 14. The applied energy produces a current through the tissue, as well as a voltage between the electrodes 12 and 14, which is conveyed to the impedance monitoring circuit 100 along conductors 92 and 94. The impedance monitoring circuit 100 determines the impedance of the tissue. The first differentiator circuit 102 produces a first time-based derivative impedance signal dz/dt that can be used to regulate the energy supplied to the tissue. The derivative signal dz/dt is indicative of the slope of the characteristic tissue impedance curve associated with the particular tissue located at the surgical site. The measured tissue impedance is a mechanical impedance that increases, over at least a portion of the characteristic impedance curve, with increasing levels of energy. As noted above, steam can be generated upon the vaporization of intracellular fluid when the applied energy and/or tissue temperature reaches a certain level. Thus, the first derivative signal dz/dt can be used to regulate the power to detect the effects of energy on the tissue, and more specifically to maintain the measured tissue impedance or the amount/level of steam generated during the electrosurgical procedure within a selected range. Typically, this range is below that level of steam that would cause the tissue to burst, and below the measured tissue impedance associated with that steam level.

In further operation, and according to another practice of the invention, a second differentiator circuit 104 can be employed to produce a second time-based derivative output signal $d^2z/(dt)^2$, which regulates the level of power supplied to the tissue based on the level of steam at the surgical site. As noted above, the second derivative output signal filters the slope changes associated with changing impedance of the tissue when heated, while identifying the presence of steam. Thus, the second differentiator circuit 104 generates a feedback, regulating output signal that regulates the power supplied to the tissue to maintain the levels of steam below a certain level or within a certain range.

Referring again to FIG. 2, the illustrated ultrasonic transducer 20 is preferably mounted on the surgical tool proximal to the energy-delivering electrode 12. However, those of ordinary skill will recognize that the transducer can also be remotely located from the electrode 12 and the surgical tool. The transducer 20 can have any particular shape or size since the exact dimensions of the transducer are not critical to the operation of the transducer in conjunction with the illustrated feedback circuit 10. The transducer 20 can be made of a piezoelectric material or from a polyvinylidine fluoride film (PVDF), and preferably is made from a piezoelectric ceramic crystal, e.g., lead zirconate-titanate, having a response frequency in the range of about 1 MHz to about 40 MHz. Other ultrasonic transducer types and configurations can also be employed in accord with the teachings of the present invention. As is known, the higher the frequency the better the resolution for near field effects. The ultrasonic transducer 20 can be mounted to the surgical tool and/or electrode by any suitable means, such as by epoxy cement.

According to one embodiment, the illustrated acoustic stage 50 can include a processor circuit 120, an acoustical analyzer circuit 130, a conventional display device 140, such as a monitor, printer or other suitable display apparatus, and a pulse generator 150. The pulse generator 150 generates an electrical pulse having a selected duration and frequency that is transferred to the transducer 20 along conductor 152. The conductor can be attached to the transducer by any suitable conventional means, such as soldering, ultrasonic welding, cold welding and the like. The output electrical pulses generated by the pulse generator can be amplified by a conventional pulse amplifier circuit 155 prior to introduction to the transducer 20.

The illustrated pulse generator 150 generates electrical pulses at selected intervals to induce the piezoelectric transducer 20 to resonate and thus emit ultrasonic energy. The emitted ultrasonic energy is directed towards the surgical site and is reflected back by the tissue and gas components at the site. The reflected waves stimulate the transducer to produce output electrical signals that are conveyed along conductor 122 to the processor circuit 120. The amplitude or intensity of the reflected ultrasound waves is indicative of the nature of the material reflecting the beam. For example, a sorer material absorbs more ultrasound energy than a harder material, and vapor or steam present at the surgical site strongly reflects ultrasound energy. Thus, the amplitude of the reflected beam is used to characterize and/or identify the specific materials at the surgical site, as well as to detect the presence of one or more materials. The interval between consecutive pulses generated by the generator is preferably sufficient to allow the ultrasonic transducer to receive reflected ultrasonic echoes resulting from the transmitted ultrasonic pulses and to transmit electrical signals to the processor circuit 120 in response to those ultrasonic echoes before transmitting another ultrasonic pulse signal.

With further reference to FIG. 2, the processor circuit 120 processes the output electrical signal produced by the transducer 20 and conveys the signal along conductor 124 to the ultrasonic analyzer circuit 130. The analyzer circuit analyzes the information contained in the output electrical signal to determine a variety of parameters, including the types of materials located at the surgical site. The analyzer circuit 130 then passes the processed signal along conductor 128 to the display 140. The display device is any conventional device that displays the electrical signals in a human readable format, and include a monitor, such as an ultrasonograph, or an oscilloscope. Those of ordinary skill in the art will recognize that the processor circuit 120 and the analyzer circuit 130 are conventional devices, and that they can be combined together, or with the pulse generator 150, in a single conventional unit, as is readily apparent to those of ordinary skill.

The ultrasonic energy transmitted by the transducer 20 is preferably a diagnostic level of energy rather than a therapeutic level of energy. The ultrasonic transducer 20 and the associated processing circuitry (e.g., processor 120, analyzer 130 and display 140) preferably are used to determine the affects of heating on tissue, and more specifically to determine and/or monitor the presence of steam at the surgical site.

In operation, the pulse generator 150 emits an electrical pulse along conductor 152 to the transducer 20. The transducer, in response, resonates and emits ultrasonic energy having a selected frequency. Preferably, the energy emitted is a diagnostic rather than a therapeutic level of energy. The ultrasonic energy is reflected partly by the tissue and partly by any surrounding gas, e.g., steam, that is present at the surgical site. The reflected ultrasound energy is received by the transducer, which then produces electrical signals corresponding to the intensity of the reflected ultrasonic energy. The electrical signals are carried by conductor 122 to the processor analyzer circuit 120 and 130, respectively, and then carried along conductor 128 to the display 140. The clinician can thus monitor the effects of heating on the tissue, and specifically monitor steam levels at the site. If the levels of steam are above a selected level or outside of a selected range, the analyzer circuit 130 can regulate the application of energy to the tissue by outputting a feedback signal along conductor 132 to the RF generator 40. For example, reducing or eliminating the application of energy allows the tissue to reabsorb the steam, thus reducing the likelihood that tissue will be damaged from the excess accumulation of this gas.

Figure 3:
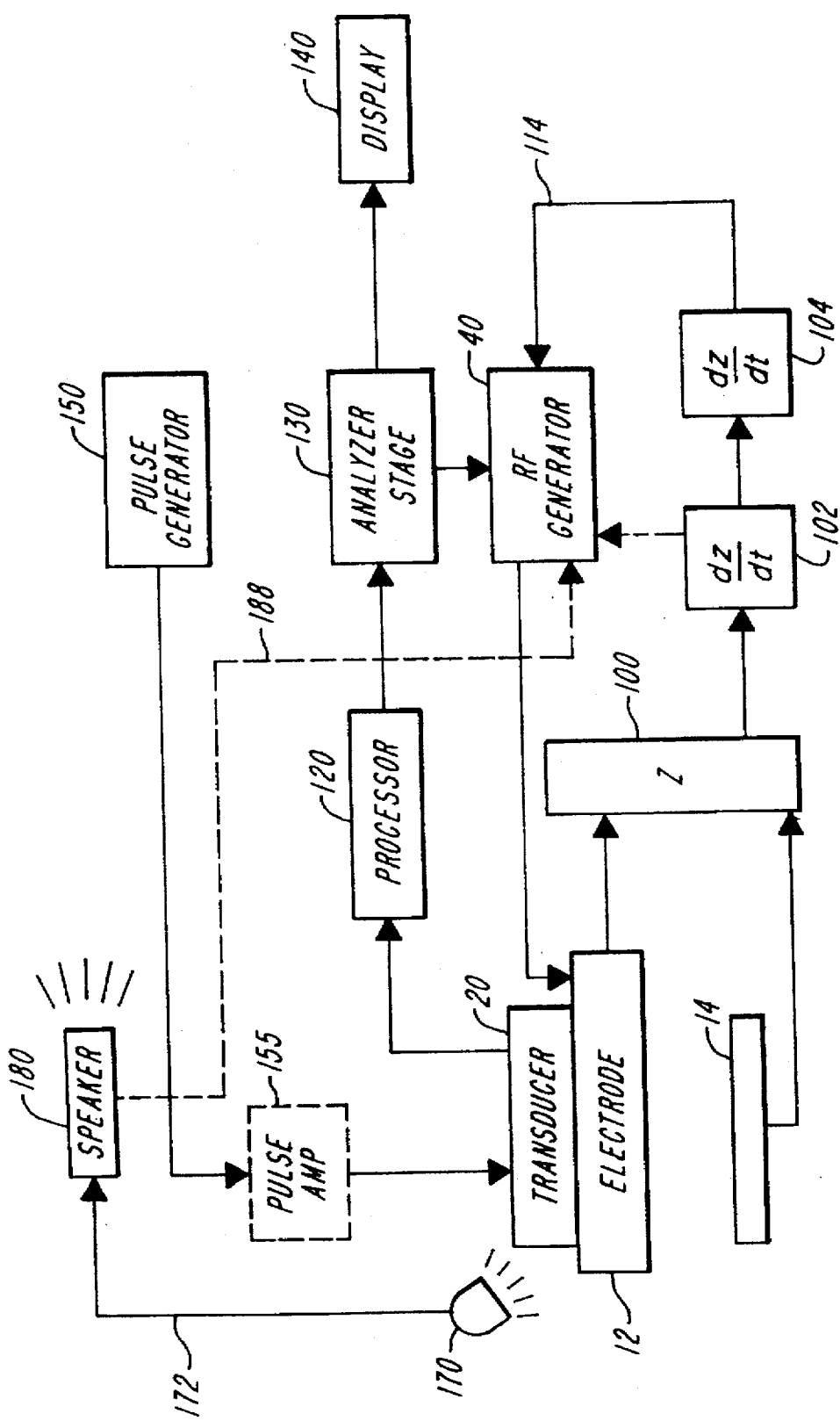
FIG. 3 is a schematic depiction of the feedback system of FIG. 2 employing a microphone.

According to still another embodiment, as shown in FIG. 3, a microphone 170 can be mounted on the surgical tool adjacent the electrode 12 and/or the transducer 20. The microphone 170 detects sound at the surgical site and converts the sound to electrical signals that are carried along conductor 172 to a speaker 180. The speaker 180 transforms the electrical signals generated by the microphone into audible signals that are emitted thereby. An acoustic analyzer circuit can be disposed between the microphone 170 and speaker 180 to analyze the acoustic waves received by the microphone 180. The circuit preferably determines the changing data (e.g., changing amplitudes of the waves and the spectral data) of the acoustic waves. The analyzer circuit can generate an output signal that is conveyed to the generator 40 to regulate the amount of energy supplied to the electrode 12. The microphone and speaker are conventional items that are known to those of ordinary skill. Those of ordinary skill in the art will also recognize that the microphone need not be mounted on the surgical tool, but rather can be carried or mounted separately at the surgical site. Furthermore, the speaker 180 can be integrated with the acoustic analyzer circuit.

Although illustrated as the speaker output signal functioning to regulate the generator 40, the electrical output signals of the microphone, the audible signals of the speaker, and/or the output signal of the analyzer circuit can be employed to regulate the amount of energy delivered to the energy-delivering electrode 12 via conductor 188. Referring again to FIG. 3, the electrical output signal on conductor 188 can be conveyed to the generator 40 along conductor 188. The generator, in response to the magnitude of the signal, can regulate the amount of power supplied to the energy-delivering electrode 12. Appropriate electrical circuitry to condition and magnify the electrical output signals generated by the microphone/speaker can also be employed. Those of ordinary skill will readily recognize the appropriate circuitry that can be employed to effectuate the necessary conditioning and analyzing of the output regulating signal.

In operation, the RF generator 40 applies energy to the tissue through the energy-delivering electrode 12. The heating of the tissue induces certain biological changes, including vaporization of the intracellular fluids, blanching, and desiccation. The creation of steam at the surgical site also produces characteristic sounds that are detected by the microphone 170 and conveyed to the clinician by the speaker 180. According to one practice, the creation of high levels of steam have associated therewith higher levels of noise, and vice versa. Thus, the clinician can audibly monitor the relative levels of steam by monitoring the sound levels associated therewith. The power supplied by the generator 40 to the electrode 12 can then be regulated by either the clinician, via a switch or knob mounted on the generator or a foot pedal coupled thereto, or by the feedback signals conveyed along conductor 188 generated by either the microphone, speaker or acoustic analyzer circuit.

The surgical tools employed with the electrosurgical feedback system 10 of the invention are varied, and can include cooling apparatus for regulating the temperature of the electrode to optimize the magnitude of heat transfer between the electrode and the tissue, and to provide for the deeper penetration of heat energy. Surgical tools employing a cooling mechanism are known in the art, and described in U.S. Pat. No. 5,334,193 of Nardella, which is herein incorporated by reference.

While the preceding description has been presented with reference to the above embodiments, it is apparent to those of ordinary skill that changes and modifications can be made to the illustrated circuitry without departing from the spirit and scope of the invention. For example, those of ordinary skill will recognize that any suitable power source can be used, such as a laser. The laser can be used to pulse a transducer (such as a metallic transducer). The laser pulse can be conveyed to the transducer by one or more optical fibers. Additionally, an array of transducers can be used to produce either coherent or incoherent ultrasonic energy, rather than a single transducer.

It is also to be understood that the following claims are to cover all generic and specific features of the invention described herein, and all statements of the scope of the invention which, as a matter of language, might be said to fall therebetween.

I claim:

1. A feedback electrosurgical system for use with a surgical tool to detect the effects of energy on tissue, said system comprising a first energy-delivering electrode to be mounted to the surgical tool and adapted to deliver electrosurgical energy from a power source to tissue disposed adjacent thereto, a second electrode adapted to receive the energy delivered by the first electrode and passing through the tissue, impedance measurement means in electrical communication with the surgical tool for determining the electrical impedance of the tissue, said impedance measurement means generating an impedance output signal indicative of the tissue impedance, differentiation means in circuit with the impedance measurement means for determining the derivative of the tissue impedance in response to the impedance output signal, said differentiation means generating a derivative output signal indicative of the formation of gas created during application of energy to tissue, and power regulation means in circuit with the differentiation means and the power source for regulating the application of electrosurgical energy by the power source to the energy-delivering electrode in response to the derivative output signal.

2. The electrosurgical system of claim 1 wherein the differentiation means includes first differentiation means in communication with the impedance measurement means for determining the first time-based derivative of the impedance output signal, said first differentiation means generating a first derivative output signal in response to the impedance output signal, and wherein the power regulation means regulates the application of energy to the energy-delivering electrode in response to the first derivative output signal.

3. The electrosurgical system of claim 1 further comprising acoustical detection means, coupled to the surgical tool and the power regulation means, for acoustically detecting the effects of energy on tissue, said acoustical detection means generating an acoustic output signal indicative of the formation of gas created during application of energy to tissue, wherein the power regulation means regulates the application of energy to the energy-delivering electrode in response to at least one of the derivative output signal and the acoustic output signal.

4. The electrosurgical system of claim 3 wherein said acoustical detection means includes ultrasound means for ultrasonically detecting the heating effects of energy on tissue.

5. The electrosurgical system of claim 4 wherein the ultrasound means comprises an ultrasonic transducer that is mounted on a distal end of the surgical tool.

6. The electrosurgical system of claim 5 wherein the ultrasonic transducer is mounted in close proximity to the energy-delivering electrode.

7. The electrosurgical system of claim 5 wherein the ultrasonic transducer is a piezoelectric ceramic crystal.

8. The electrosurgical system of claim 7 wherein the acoustical detection means further comprises pulse means coupled to the ultrasound means for electrically activating the ultrasound means to emit ultrasonic pulses having a selected frequency and a selected duration.

9. The electrosurgical system of claim 8 wherein the emitted ultrasonic pulses are reflected by one of the tissue and the gas formed during the application of energy to tissue, and wherein the acoustical detection means further comprises receiver means coupled to the ultrasound means for generating the acoustic output signal in response to the reflected ultrasonic pulses.

10. The electrosurgical system of claim 9 further comprising display means coupled to the receiver means for displaying the reflected ultrasonic pulses.

11. The electrosurgical system of claim 3 wherein the acoustical detection means includes microphone means for detecting sounds associated with the application of energy to tissue, and for generating an electrical output signal corresponding to the detected sounds.

12. The electrosurgical system of claim 11 wherein the acoustical detection means further includes speaker means coupled to the microphone means for producing an audible output signal in response to the electrical output signal.

13. The electrosurgical system of claim 1 wherein the power source is one of an RF generator, a laser and an ultrasonic energy source.

14. A feedback electrosurgical system for use with a surgical tool to detect the effects of energy on tissue, said system comprising a first energy-delivering electrode to be mounted to the surgical tool and adapted to deliver electrosurgical energy from a power source to tissue disposed adjacent thereto, a second electrode adapted to receive the energy delivered by the first electrode and passing through the tissue, impedance measurement means in electrical communication with the surgical tool for determining the electrical impedance of the tissue, said impedance measurement means generating an impedance output signal indicative of the tissue impedance, differentiation means in circuit with the impedance measurement means for determining the derivative of the tissue impedance in response to the impedance output signal, said differentiation means generating a derivative output signal indicative of the time-based derivative of the impedance output, wherein the differentiation means comprises:

first differentiation means in communication with the impedance measurement means for determining the first time-based derivative of the impedance output signal, said first differentiation means generating a first derivative output signal in response to the impedance output signal, and second differentiation means in circuit with the first differentiation means for determining the second time-based derivative of the impedance output signal, said second differentiation means generating a second derivative output signal in response to the first derivative output signal, and power regulation means in circuit with the differentiation means and the power source for regulating the application of electrosurgical energy by the power source to the energy-delivering electrode in response to the derivative output signal, the power regulation means regulating the application of energy to the energy-delivering electrode in response to the second derivative output signal.

15. An electrosurgical feedback system for use with a surgical tool to detect the effects of energy on tissue, said system comprising a first energy-delivering electrode to be mounted to the surgical tool and adapted to receive electrosurgical energy from a power source and deliver energy to the tissue, a second electrode adapted to receive the energy delivered by the first electrode and passing through the tissue, acoustical detection means coupled to the surgical tool for detecting acoustically the effects of energy on the tissue, said acoustical detection means generating an acoustic output signal indicative of the formation of gas created during application of energy to the tissue, and power regulation means in circuit with the surgical tool and the acoustical detection means for regulating the energy supplied to the energy delivering electrode in response to the acoustic output signal.

16. The electrosurgical system of claim 15 wherein the acoustical detection means includes an ultrasonic transducer.

17. The electrosurgical system of claim 16 wherein the acoustical detection means further includes pulsing means coupled to the ultrasonic transducer for applying an electrical current thereto to induce the transducer to generate ultrasonic pulses.

18. The electrosurgical system of claim 17 wherein the acoustical detection means further comprises processor means coupled to the ultrasonic transducer for receiving and processing electrical signals generated by the ultrasonic transducer that are indicative of reflected ultrasonic pulses, said processor means generating the acoustic output signal.

19. The electrosurgical system of claim 18 further including display means in circuit with the processor means for displaying the reflected ultrasonic pulses.

20. The electrosurgical system of claim 15 further comprising impedance measurement means coupled to the surgical tool for determining the impedance of the tissue disposed between the energy receiving electrode and the second electrode, said impedance measurement means generating an impedance output signal indicative of the impedance of the tissue.

21. The electrosurgical system of claim 20 further comprising first derivative means coupled to the impedance measurement means for determining the first time-based derivative of the impedance output signal, said first derivative means generating a first derivative output signal indicative of the first derivative of the tissue impedance.

22. The electrosurgical system of claim 21 further including means for communicating the first derivative output signal to said power regulation means, said power regulation means regulating the power supplied to the energy-delivering electrode in response to at least one of the first derivative output signal and the acoustic output signal.

23. The electrosurgical system of claim 15 wherein the acoustical detection means includes microphone means for detecting the effect of energy on the tissue, said microphone means generating an electrical output signal indicative of sounds associated with the heating of tissue.

24. The electrosurgical system of claim 23 further comprising speaker means in communication with the microphone means for converting said electrical output signal of said microphone means into an audible output signal.

25. An electrosurgical feedback system for use with a surgical tool to detect the effects of energy on tissue, said system comprising a first energy-delivering electrode to be mounted to the surgical tool and adapted to receive electrosurgical energy from a power source and deliver energy to the tissue, a second electrode adapted to receive the energy delivered by the first electrode and passing through the tissue, acoustical detection means coupled to the surgical tool for detecting acoustically the effects of energy on the tissue, said acoustical detection means generating an acoustic output signal indicative of the heating effects on the tissue, and power regulation means in circuit with the surgical tool and the acoustical detection means for regulating the energy supplied to the energy delivering electrode in response to the acoustic output signal, impedance measurement means coupled to the surgical tool for determining the impedance of the tissue disposed between the energy receiving electrode and the second electrode, said impedance measurement means generating an impedance output signal indicative of the impedance of the tissue, first derivative means coupled to the impedance measurement means for determining the first time-based derivative of the impedance output signal, said first derivative means generating a first derivative output signal indicative of the first derivative of the tissue impedance, second derivative means in communication with the first derivative means and the power regulation means for determining the derivative of the first derivative output signal, said second derivative means generating a second derivative output signal indicative of the second derivative of the impedance output signal.

26. The electrosurgical system of claim 25 including means for communicating the second derivative output signal to said power regulation means, said power regulation means regulating the power supplied to the energy-delivering electrode in response to at least one of the second derivative output signal and the acoustic output signal.

27. The electrosurgical system of claim 26 further including display means for displaying at least one of the first derivative output signal, the second derivative output signal and the acoustic output signal.

28. An electrosurgical feedback system for use with a surgical tool to detect the effects of energy on tissue, said system comprising a first energy-delivering electrode to be mounted to the surgical tool and adapted to receive electrosurgical energy from a power source and deliver energy to the tissue, a second electrode adapted to receive the power delivered by the first electrode and passing through the tissue, acoustical detection means associated with a surgical tool and remotely located relative thereto for detecting acoustically the effects of energy on the tissue, said acoustical detection means generating an acoustic output signal indicative of the formation of gas created during application of energy to the tissue, and power regulation means in circuit with the acoustical detection means for regulating the power supplied to the tool in response to the acoustic output signal.

29. The electrosurgical system of claim 28 wherein the acoustical detection means further includes an ultrasonic transducer and pulsing means coupled to the ultrasonic transducer for applying an electrical current thereto to induce the transducer to generate ultrasonic pulses.

30. The electrosurgical system of claim 29 wherein the acoustical detection means further comprises processor means coupled to the ultrasonic transducer for receiving and processing electrical signals generated by the ultrasonic transducer that are indicative of reflected ultrasonic pulses, said processor means generating the acoustic output signal.

31. The electrosurgical system of claim 28 wherein the acoustical detection means includes microphone means for detecting the effect of energy on the tissue, said microphone means generating an electrical output signal indicative of sounds associated with the heating of tissue.

32. The electrosurgical system of claim 31 further comprising speaker means in communication with the microphone means for converting said electrical output signal of said microphone means into an audible output signal.

33. A feedback electrosurgical system for detecting the effects of energy on tissue and for use with a surgical tool comprising a first energy-delivering electrode to be mounted to the surgical tool and adapted to deliver electrosurgical energy from a power source to tissue disposed adjacent thereto and a second electrode adapted to receive the energy delivered by the first electrode and passing through the tissue, the system comprising:

impedance measurement means in electrical communication with the surgical tool for determining the electrical impedance of the tissue, said impedance measurement means generating an impedance output signal indicative of the tissue impedance, differentiation means in circuit with the impedance measurement means for determining the derivative of the tissue impedance in response to the impedance output signal, said differentiation means generating a derivative output signal indicative of the formation of gas created during application of energy to tissue, and power regulation means in circuit with the differentiation means and the power source for regulating the application of electrosurgical energy by the power source to the energy-delivering electrode in response to the derivative output signal.

34. An electrosurgical feedback system for detecting the effects of energy on tissue and for use with a surgical tool comprising a first energy-delivering electrode to be mounted to the surgical tool and adapted to receive electrosurgical energy from a power source and deliver energy to the tissue and a second electrode adapted to receive the energy delivered by the first electrode and passing through the tissue, the system comprising:

acoustical detection means coupled to the surgical tool for detecting acoustically the effects of energy on the tissue, said acoustical detection means generating an acoustic output signal indicative of the formation of gas created during application of energy to the tissue, and power regulation means in circuit with the surgical tool and the acoustical detection means for regulating the energy supplied to the energy delivering electrode in response to the acoustic output signal.

* * * * *